United States Patent [19]

Abreu et al.

[11] Patent Number: 5,063,245

[45] Date of Patent: Nov. 5, 1991

[54] CORTICOTROPIN-RELEASING FACTOR ANTAGONISM COMPOUNDS

[75] Inventors: Mary E. Abreu, Baltimore; Waclaw Rzeszotarski, Millersville; Donald J. Kyle, Baltimore; Roger N. Hiner, Baltimore; Richard L. Elliott, Baltimore, all of Md.

[73] Assignee: Nova Pharmaceutical Corporation, Baltimore, Md.

[21] Appl. No.: 500,478

[22] Filed: Mar. 28, 1990

[51] Int. Cl.$^5$ .................. A61K 31/415; C07D 231/22
[52] U.S. Cl. ..................................... 514/404; 548/365
[58] Field of Search ......................................... 548/365

[56] References Cited

FOREIGN PATENT DOCUMENTS 2726784 12/1977 Fed. Rep. of Germany .

Primary Examiner—Robert W. Ramsuer
Attorney, Agent, or Firm—Vincent L. Fabiano

[57] ABSTRACT

The present invention relates to a method of producing corticotropin-releasing factor (CRF) antagonist activity and thus provides a method of treating a wide range of stress-related disorders, including affective illnesses, such as depression and anxiety, as well as irritable bowel syndrome, anorexia nervosa, cardiovascular abnormalities and stress-induced immune suppression. The invention also relates to compounds (4-substituted thio-5-oxo-3-pyrazolines) and to pharmaceutical compositions suitable for use in such a method.

8 Claims, No Drawings

CORTICOTROPIN-RELEASING FACTOR ANTAGONISM COMPOUNDS

BACKGROUND OF THE INVENTION

1. Technical Field

This invention relates to a method of producing corticotropin-releasing factor (CRF) antagonism employing certain 4-substituted thio-5-oxo-3-pyrazolines. The invention further relates to compounds and pharmaceutical compositions suitable for use in such a method.

2. Background Information

Although the existence of a "corticotropin releasing factor" was postulated more than 30 years ago [G. W. Harris, Physiol. Rev., 28, 139 (1948)], it was not until 1981 that the purification and sequencing of this hormone was accomplished [J. Spiess et al., Proc. Natl. Acad. Sci. U.S.A., 78, 6517 (1981); W. Vale et al., Science, 213, 1394 (1981)]. This CRF isolated from ovine hypothalmi was identified as a 41 residue straight chain peptide. Shortly thereafter the sequences of human and rat CRF were determined. They were the same, but differed from ovine CRF (oCRF) in 7 of the 41 amino acid residues [J. Rivier et al., Proc. Natl. Acad. Sci., U.S.A., 80, 4851(1983); Furutani et al., Nature, 301, 537 (1983)].

Both types of CRF produce profound alterations in behavioral and autonomic nervous system function [G. F. Koob and F. E. Bloom, Fed. Proc., 44, 259 (1985); M. R. Brown and L. A. Fisher, Fed. Proc., 44, 243 (1985)]. When administered directly into the brain, CRF initiates behavioral, physiological and endocrine responses that are essentially identical to those observed when animals are exposed to a stressful environment. For example, intracerebroventricular (icv) injection of CRF elicits behavioral activation [R. E. Sutton et al., Nature, 297, 331 (1982)], produces a long-lasting activation of the electroencephalogram [C. L. Ehlers et al., Brain Res., 278, 332 (1983)], stimulates the sympathoadrenomedullary pathway [e.g., M. R. Brown et al., Endocrinology, 110, 928 (1982)], increases heart rate and blood pressure [L. A. Fisher et al., Endocrinology, 110, 2222 (1982)], increases oxygen consumption [M. R. Brown et al., Life Sciences., 30, 207 (1982)], alters gastrointestinal activity [C. L. Williams et al., Am. J. Physiol., 253, G582 (1987)], suppresses food consumption [A. S. Levine et al., Neuropharmacology, 22, 337 (1983)] and sexual behavior [D. J. S. Sirinathsinghji et al., Nature, 305, 232 (1983)] and compromises immune function [M. Irwin et al., Am. J. Physiol., 255, R744 (1988)].

CRF antagonists would be expected to reverse the effects of CRF administration. CRF antagonists identified to date are restricted to peptides [C. L. Rivier, J. E. F. Rivier, W. W. Vale, Jr., and M. R. Brown, U.S. Pat. No. 4,605,642, Aug. 12, 1986; J. Rivier, C. Rivier, and W. Vale, Science, 224, 889 (1984)]. A relatively potent antagonist of CRF is α-helical CRF$_{9-14}$. Evaluation of this antagonist in a host of in vitro and in vivo model systems has established the physiological role of CRF, not only in the control of corticotropin (ACTH) secretion and other proopiomelanocortin (POMC) gene products from the anterior pituitary gland, but more importantly, in the direct mediation of behavioral and physiological responses to stress [A. Tazi et al., Regul. Peptides, 18, 37 (1987); M. R. Brown et al., Regul. Peptides, 16, 321 (1986); C. L. Williams et al., Am. J. Physiol, 253, G582 (1987)].

Thus, the evidence that a CRF antagonist can attenuate the pharmacological responses to CRF is compelling and establishes the potential therapeutic utility of the compounds and compositions of this invention.

OBJECTS OF THE INVENTION

It is a general object of the present invention to provide a method of producing CRF antagonism and thus to provide a method of treating, for example, a wide range of stress-related disorders. It is a further object of the invention to provide compounds and pharmaceutical compositions suitable for use in such a method.

Further objects and advantages of the invention will be clear to one skilled in the art from a reading of the description that follows.

SUMMARY OF THE INVENTION

The present invention relates to a method of producing CRF antagonist activity and thus provides a method of treating, for example, a variety of stress-related disorders, including affective illnesses, such as depression and anxiety, as well as irritable bowel syndrome, anorexia nervosa, cardiovascular abnormalities and stress-induced immune suppression. The invention also relates to compounds (4-substituted thio-5-oxo-3-pyrazolines) and to pharmaceutical compositions suitable for use in such a method.

DETAILED DESCRIPTION OF THE INVENTION

The present invention relates to a method of producing CRF antagonism and to compounds (4-substituted thio-5-oxo-3-pyrazolines) and compositions suitable for use in such a method. The 4-substituted thio-5-oxo-3-pyrazolines, which serve as the active ingredient of the pharmaceutical compositions of the present invention, are represented by Formula I and Formula II:

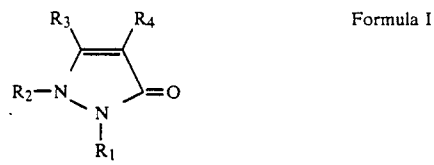

Formula I

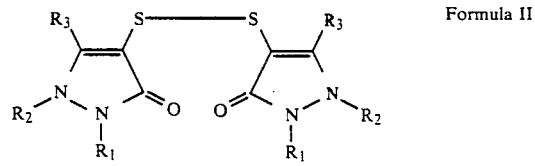

Formula II wherein:

$R_1$ is hydrogen; phenyl; phenyl singly or multiply substituted with halogen, nitro, amino, alkylamino (advantageously $C_{1-4}$), dialkylamino (advantageously $C_{1-4}$), dialkylaminomethyl (advantageously $C_{1-4}$), $C_{1-8}$alkyl (straight chain, branched, cyclic, saturated or unsaturated), hydroxy, alkoxy (advantageously $C_{1-4}$), cyano, trifluoromethyl, alkylthio (advantageously $C_{1-4}$), alkylsulfonyl (advantageously $C_{1-4}$), or methylenedioxy; thienyl; pyridyl; chloropyridyl; benzofuranyl; naphthyl; indolyl; indanyl; indenyl; $C_{1-8}$alkyl (straight chain, branched, cyclic, saturated or unsaturated); or aralkyl (where the aryl group is selected from those set forth immediately above and the alkyl group is $C_{1-3}$; and $R_2$ is $C_{1-8}$alkyl (straight chain, branched, cyclic, saturated or unsaturated), phenyl or aralkyl (where the aryl group is selected from those set forth in the definition of $R_1$ and the alkyl group is $C_{1-3}$;

$R_3$ is $C_{1-8}$alkyl (straight chain, branched, cyclic, saturated or unsaturated); $C_{1-8}$ straight chain alkyl substituted with at least one carboxylic acid, amino or carboxymethoxy group; amino; alkylamino (advantageously $C_{1-4}$); dialkylamino (advantageously $C_{1-4}$); pyrrolidinyl; piperidinyl; piperazinyl; 4-methylpiperazinyl; morpholinyl; thiomorpholinyl; aminomethyl; alkylaminomethyl (advantageously $C_{1-4}$); dialkylaminomethyl (advantageously $C_{1-4}$); pyrrolidinylmethyl; piperidinylmethyl; 4-methylpiperazinylmethyl; morpholinylmethyl; thiomorpholinylmethyl; phenyl; or phenyl singly or multiply substituted with acetimido, amino, nitro, alkylamino (advantageously $C_{1-4}$), dialkylaminomethyl (advantageously $C_{1-4}$), hydroxy, alkoxy (advantageously $C_{1-4}$), alkylsulfonyl (advantageously $C_{1-4}$), methylenedioxy, halogen or trifluoromethyl;

$R_4$ is SCN, $SCO$-$C_{1-6}$alkyl, $SCCl_3$, or $SCF_3$.

In addition to the above, the compound 2,3-dimethyl-5-oxo-1-phenyl-3-pyrazolin-4-yl thioacetate can also be used in the claimed method and composition.

Pharmaceutically acceptable salts of the above-described compounds can be used in the compositions and method to which the invention relates.

Certain of the compounds described above are known in the art [see specifically compounds disclosed in: H. P. Kaufman et al., Chem. Ber., 56,2514 (1923); F. v. Konek, Chem. Ber. 53,1667 (1920); Japanese Patent 12,664 (1964), M. Ochiai Chem. Abstr., 61, 16072c (1964)]. The remaining compounds are believed to be disclosed for the first time herein.

Preferred compounds of Formula I for use in the present method and compositions have the following substituents:

$R_1$ is phenyl, 4-substituted phenyl, 2-naphthyl, benzyl or 3,4-$Cl_2C_6H_3$;

$R_2$ and $R_3$ are, independently, methyl or ethyl; and $R_4$ is SCN or $SCOCH_3$.

Preferred compounds of Formula II have as substituents at $R_1$, $R_2$ and $R_3$, those set forth immediately above in relation to the preferred compounds of Formula I.

The most preferred compounds for use in the method and compositions of the invention are those of Formula I where: (i) $R_1=4$-$CH_3$phenyl, $R_2=R_3=$methyl, and $R_4=$SCN; (ii) $R_1=4$-$OCH_3$phenyl, $R_2=$methyl, $R_3=$ethyl, and $R_4=$SCN; and (iii) $R_1=4$-$CH_3SO_2$phenyl, $R_2=$ethyl, $R_3=$methyl, and $R_4=$SCN.

Details of procedures suitable for preparing certain of the above compounds of Formulas I and II have been described by H. P. Kaufman and J. Liepe [Chem. Ber., 56, 2514–2520 (1923)] and F. v. Konek [Chem. Ber., 53, 1667–1671 (1920)]. For example, these references teach that, in the case of certain of the compounds of Formula I disclosed therein, an appropriately substituted hydrazine is condensed with an ethyl ketoacetate to give a substituted 5-oxo-2-pyrazoline which is treated with an alkyl or benzyl halide to afford the corresponding 2-alkyl- or benzyl-5-oxo-3-pyrazoline. The resulting 1,2,3-trisubstituted 5-oxo-3-pyrazoline, such as antipyrine, is treated with bromine and potassium thiocyanate in a solvent such as acetic acid. These references also disclose that, in the case of the disulfides of Formula II, several different methods of preparation can be employed which make use of the thiocyanates of Formula I, or related compounds, in which the 4-position is not substituted. For example, the substituted 3-methyl-5-oxo-3-pyrazolin-4-yl thiocyanate is converted to the corresponding disulfide by hydrogenation in the presence of a suitable catalyst, such as palladium. A second method for converting the substituted 3-methyl-5-oxo-3-pyrazolin-4-yl thiocyanate to disulfide entails treatment with a base, such as potassium hydroxide, in a suitable solvent, for example, aqueous dimethyl sulfoxide. Another route involves treatment of an appropriately substituted 3-methyl-5-oxo-3-pyrazoline, such as antipyrine, with sulfur monochloride ($S_2Cl_2$).

Newly disclosed compounds can be prepared using methods known in the art (see also methods set forth in the Examples that follow).

The compounds of this invention are generally utilized as the free base or as acid addition salts having the utility of the free base. Such salts, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric or nitric acids.

The compounds of the invention can be administered in a variety of pharmaceutical preparations well known to those skilled in the pharmaceutical art. For parenteral administration, the compounds can be prepared in aqueous injection solutions (sterile) which can contain antioxidants, buffers, bacteriostats, and other additives commonly employed in such solutions. Extemporaneous injection solutions can be prepared from sterile pills, granules or tablets which can contain diluents, dispersing and surface active agents, binders, and lubricants, as well as a compound of the invention.

In the case of oral administration, fine powders or granules of the compound of the invention can be formulated with diluents and dispersing and surface active agents, and can be prepared in water, a syrup, capsules, cachets, a non-aqueous suspension or an emulsion. In dry forms, optional binders and lubricants can be present. The compositions may also include flavorants, preservatives, suspending, thickening and emulsifying agents and other pharmaceutically acceptable additives. Granules or tablets for oral administration can be coated.

The pharmaceutical compositions of the invention, which can be used in the method of producing antagonism of CRF, comprise a pharmaceutically acceptable carrier and, as the active ingredient, at least one of the above-described 4-substituted thio-5-oxo-3-pyrazolines. The active ingredient is present in the dosage unit composition in an amount sufficient to produce the CRF antagonist activity, yet in an amount that is not unacceptably toxic to the user. Preferably, the pharmaceutical compositions of the invention include the active ingredient in a quantity selected from 1 mg to 500 mg, advantageously, from about 2 mg to 100 mg, per dosage unit, depending upon the route of administration. Appropriate concentrations and dosage unit sizes can be readily determined by one skilled in the art. Advantageously, equal doses will be administered, preferably, between one and four times per day.

As indicated above, the compounds of the invention display novel activity at the CRF receptor site and therefore represent novel therapeutic agents for the treatment of a wide range of stress-related disorders. For example, evidence from a variety of sources indicates that the use of centrally-active CRF receptor antagonists can be used for the treatment of depression. In addition, substantial data indicate that such compounds can be useful in the treatment of a number of other stress-related disorders including anxiety, panic disorder, obsessive-compulsive disorder, abnormal aggression, stress-induced cardiovascular abnormalities (e.g., unstable angina and reactive hypertension), anorexia nervosa, bulimia and irritable bowel syndrome. CRF antagonists also find utility in treating psychologically or physically induced stress-mediated immune suppression associated with a number of disease states. It is expected that CRF antagonists would be useful in ameliorating symptoms of alcohol and drug withdrawal and in treating epilepsy.

The compounds of this invention demonstrate CRF receptor affinity in binding studies that measure their ability to inhibit the specific binding of [$^{125}$I]tyrosine-oCRF to rat cerebral cortex membranes. CRF antagonist activity is established by the ability of the compounds to antagonize CRF-stimulated adenylate cyclase activity, it having been established that CRF receptors are coupled to a guanine nucleotide regulatory protein that activates adenylate cyclase [G. Aguilera et al., Neuroendocrinology, 43, 79 (1986); G. Battaglia et al., Synapse, 1, 572 (1987)].

The following non-limiting Examples, in which temperature is given in degrees Celcius, describe the invention in greater detail.

EXAMPLE 1

Substituted 1-Aryl-3-Methyl-5-Oxo-3-Pyrazolin-4-yl Thiocyanates

1-Aryl-3-Methyl-5-Oxo-2-Pyrazoline

One equivalent of the arylhydrazine hydrochloride, ethyl acetoacetate and sodium acetate were heated at 100° C. for 3-15 hours, then the crude product was isolated by adding chloroform, filtering and concentrating the filtrate. Purification via chromatography afforded the pure 1-aryl-3-methyl-5-oxo-2-pyrazoline (50-80%).

2-Alkyl-1-Aryl-3-Methyl-5-Oxo-3-Pyrazoline

A mixture of the 1-aryl-3-methyl-5-oxo-3-pyrazoline and the appropriate alkyl iodide was heated in a sealed tube at 100°-150° C., for 16 hours. After being cooled to 20° C., the reaction mixture was diluted with 1N sodium hydroxide and extracted with methylene chloride to yield the crude product. Chromatography (silica) afforded the pure 2-alkyl-1-aryl-3-methyl-5-oxo-3-pyrazoline (60-80%).

2,3-Dimethyl-5-Oxo-1-Phenyl-3-Pyrazolin-4-yl Thiocyanate

Bromine (5.1 mL, 0.102 mol) was added dropwise to a chilled (0° C.) solution of antipyrine (18.80 g, 0.10 mol) and potassium thiocyanate (9.70 g, 0.10 mol) in acetic acid (1 L). The resulting mixture was allowed to warm to room temperature and then stirred for 16 hours. The solvent was evaporated at reduced pressure and the residue was taken up in methylene chloride and neutralized with saturated aqueous sodium bicarbonate. The layers were separated and the organic phase was extracted with methylene chloride (3×75 mL) and the combined organic solutions were dried over anhydrous sodium sulfate, filtered and concentrated. The residue was recrystallized from ethyl acetate-hexane to give the product (19.6 g, 80% yield) as an off-white crystalline solid, mp 141°-143° C.

Also prepared by this general procedure were: 2-ethyl-3-methyl-5-oxo-1-phenyl-3-pyrazolin-4-yl thiocyanate (recrystallized from acetone-ether, mp 90°-91° C.); and 2-ethyl-3-methyl-5-oxo-1-(4-nitrophenyl)-3-pyrazolin-4-yl thiocyanate (recrystallized from methanol-ethyl acetate, mp 153°-155° C.).

The following thiocyanates were also prepared as described above: 2-ethyl-3-methyl-5-oxo-1-(3,4-dichlorophenyl)-3-pyrazolin-4-yl thiocyanate (recrystallized from ethyl acetatehexane, mp 132°-133° C.); 2-ethyl-3-methyl-5-oxo-1-(4-methoxyphenyl)-3-pyrazolin-4-yl thiocyanate (mp 153°-154° C.); 2-ethyl-3-methyl-5-oxo-1-(4-methylsulfonylphenyl)-3-pyrazolin-4-yl thiocyanate (recrystallized from ethyl acetate, mp 186° C.); 2,3-dimethyl-1-naphthyl-5-oxo-3-pyrazolin-4-yl thiocyanate (recrystallized from methanol-ethyl acetate-hexane, mp 205°-206° C.); 1-cyclohexyl-2,3-dimethyl-5-oxo-3-pyrazolin-4-yl thiocyanate (recrystallized from ethyl acetate-hexane, mp 125°-126.5° C.); 2,3-dimethyl-5-oxo-1-(3-cyanophenyl)-3-pyrazolin-4-yl thiocyanate (mp 164°-166° C.); 3-ethyl-2-methyl-5-oxo-1-phenyl-3-pyrazolin-4-yl thiocyanate (mp 82°-84° C.); 2-ethyl-3-methyl-5-oxo-1-(3-chlorophenyl)-3-pyrazolin-4-yl thiocyanate (recrystallized from ethyl acetate-hexane, mp 97°-98° C.); 3-methyl-5-oxo-1-phenyl-2-propyl-3-pyrazolin-4-yl thiocyanate (mp 68°-69° C.); 1,2-diethyl-3-methyl-5-oxo-3-pyrazolin-4-yl thiocyanate (recrystallized from ethyl acetate-hexane, mp 93°-94° C.); 2,3-dimethyl-5-oxo-1-(4-methylphenyl)-3-pyrazolin-4-yl thiocyanate (recrystallized from ethyl acetate, mp 170.5°-172° C.); 1,2,3-triethyl-5-oxo-3-pyrazolin-4-yl thiocyanate (mp 56°-57° C.); 2-ethyl-3-methyl-5-oxo-1-(4-nitrophenyl)-3-pyrazolin-4-yl thiocyanate (recrystallized from ethyl acetate-methanol, mp 153°-155° C.); 3-amino-2-methyl-5-oxo-1-phenyl-3-pyrazolin-4-yl thiocyanate (recrystallized from ethyl acetate, mp 231°-232° C.); 1-benzyl-2-ethyl-3-methyl-5-oxo-3-pyrazolin-4-yl thiocyanate (recrystallized from ethyl acetate-hexane, mp 95°-97° C.); 2,3-dimethyl-5-oxo-1-(2,6-dichlorophenyl)-3-pyrazolin-4-yl thiocyanate (mp 210°-213° C.); 2-benzyl-1,3-dimethyl-5-oxo-3-pyrazolin-4-yl thiocyanate, hemifumarate (recrystallized from tetrahydrofuran, mp 171°-173° C.); 2-methyl-3-mopholinomethyl-5-oxo-1-phenyl-3-pyrazolin-4-yl thiocyanate (recrystallized from acetonitrile, mp 189°-191° C.); 3-methyl-5-oxo-1-phenyl-3-pyrazolin4-yl thiocyanate (mp 132°-134° C. (dec.)); 3-methyl-5-oxo-1,2-phenyl-3-pyrazolin-4-yl thiocyanate (recrystallized from ethyl acetate-hexane, mp 169°- 173° C.); 2-methyl-5-oxo-1-phenyl-3-(3-acetamidophenyl)-3-pyrazolin-4-yl thiocyanate (recrystallized from ethyl acetate-hexane, mp 203°-204° C.); 2,3-dimethyl-5-oxo-1-(4-iodophenyl)-3-pyrazolin-4-yl thiocyanate (mp 175°-177° C.); 2,3-dimethyl-5-oxo-1-(6-chloro-2-pyridyl)-3-pyrazolinylthiocyanate (recrystallized from ethyl acetate-hexane, mp 156°-157° C.).

EXAMPLE 2

Substituted 1-Aryl-3-Methyl-5-Oxo-3-Pyrazolin-4-yl Disulfides

2,3-Dimethyl-5-Oxo-1-Phenyl-3-Pyrazolin-4-yl Disulfide

Method 1: A solution of 2,3-dimethyl-5-oxo-1-phenyl-3-pyrazolin-4-yl thiocyanate (2.5 g, 10.19 mmol) in ethyl acetate (330 mL), tetrahydrofuran (100 mL), and methanol (200 mL) was hydrogenated at an initial pressure of 60 psi of hydrogen using a Parr shaker with 10% palladium-on-carbon as the catalyst (1.6 g). After 24 hours, the reaction mixture was filtered through celite and concentrated to 150-200 mL, allowed to sit overnight, then filtered to obtain the disulfide as slightly yellow crystals (1.40 g, 63%), mp 245°-248° C.

The following disulfides were also prepared by the foregoing procedure: 2-ethyl-3-methyl-5-oxo-1-(3,4-dichlorophenyl)-3-pyrazolin-4-yl disulfide (mp 180°-180° C.); 3-ethyl-2-methyl-5-oxo-1-phenyl-3-pyrazolin-4-yl disulfide (recrystallized from ethyl acetate-hexane, mp 149°-150° C.); 2,3-dimethyl-1-naphthyl-5-oxo-3-pyrazolin-4-yl disulfide (mp 265° C. (dec.)); 1-benzyl-2-ethyl-3-methyl-5-oxo-3-pyrazolin-4-yl disulfide (mp 142°-145° C.); 2-ethyl-3-methyl-5-oxo-1-phenyl-3-pyrazolin-4-yl disulfide (recrystallized from ethyl acetate-hexane, mp 185°-187°) and 2,3-dimethyl-5-oxo-1-(6-chloro-2-pyridyl)-3-pyrazolin-4-yl disulfide (recrystallized from ethyl acetate-hexane, mp 213°-215° C.).

Method 2: A solution of 2,3-dimethyl-5-oxo-1-phenyl-3-pyrazolin-4-yl thiocyanate (2.0 g, 8.15 mmol) in dimethyl sulfoxide (35 mL), water (15 mL), and 1N potassium hydroxide (30 mL) was stirred at room temperature overnight, then the reaction mixture was diluted with water (50 mL) and extracted with methylene chloride (2×100 mL). The combined organic layers were washed with 50 mL portions of water and brine, dried (MgSO$_4$), and concentrated to afford the crude product as a yellow solid (1.2 g), mp 245°-248° C.

Method 2, as described above, was also employed to prepare 2,3-dimethyl-5-oxo-1-(4-iodophenyl)-3-pyrazolin-4-yl disulfide (mp 236.5°-238.5 ° C.) and 2-methyl-3-morpholinylmethyl-5-oxo-1-phenyl-3-pyrazolin-4-yl disulfide (mp 166°-169° C.).

Method 3: To antipyrine (20.0 g, 106.2 mmol) in glacial acetic acid (50 mL) was added sulfur monochloride (7 mL, 87.5 mmol) and the reaction mixture stirred for 24 hours at room temperature. The reaction mixture was then diluted with ice-water (300 mL) and methylene chloride (200 mL), and the pH adjusted to 12 with solid sodium hydroxide, then the aqueous layer was washed with more methylene chloride (200 mL, then 100 mL), and the combined organic layers were washed with saturated aqueous sodium bicarbonate, dried over magnesium sulfate (MgSO$_4$), and concentrated to obtain the crude product. This material was suspended in methanol (100 mL), treated with 1M ethereal hydrogen chloride (100 mL) and the solvent then evaporated to afford the disulfide as the dihydrochloride salt (10.43 g, 38%, mp 186°-188° C.).

EXAMPLE 3

2,3-Dimethyl-5-Oxo-1-Phenyl-3-Pyrazolin-4-yl Thioacetate

Procedure 1: A solution of 2,3-dimethyl-5-oxo-1-phenyl-3-pyrazolin-4-yl disulfide (8.77 g, 20 mmol) in methylene chloride (100 mL) was treated with sodium borohydride (756 mg, 20 mmol) at 25° C. After several minutes, absolute ethanol (~6 mL) was added to make the reaction mixture homogeneous. The reaction mixture was then cooled to 0° C. and small aliquots of sodium borohydride were added until TLC indicated almost complete reduction of the disulfide. The reaction mixture was then treated with pyridine (3.22 mL, 40 mmol), dimethylaminopyridine (244 mg, 2 mmol) followed by acetyl chloride (2.98 mL, 42 mmol). After 5 minutes, more pyridine (1 mL) and acetyl chloride (1 mL) were added. After an additional 15 minutes, the reaction mixture was filtered and the filtrate diluted with methylene chloride (100 mL) and the organic layer washed with saturated aqueous NaHCO$_3$ (100 mL) and brine (50 mL), dried (MgSO$_4$) and concentrated to obtain the crude product. This material was purified by column chromatography (silica, ethyl acetate/hexane 2:1) to afford the pure product as a white solid, which was converted to the hydrochloride (mp 118°-121° C.) by dissolving in ethyl acetate/ether and treating with 1M ethereal HCl (3.22, 27.8%).

Procedure 2: To a solution of 2,3-dimethyl-5-oxo-1-phenyl-3-pyrazolin-4-yl thiocyanate (620 mg, 2.52 mmol) in DMSO (7 mL) was added 10% aqueous NaOH (7 mL). After stirring for 1 hour at 25° C., methylene chloride (20 mL) was added followed by acetic anhydride (1 mL). More acetic anhydride (~2 mL) was added after 1 hour. After stirring an additional 5 minutes, the reaction mixture was diluted with methylene chloride (80 mL) and washed with 40 mL portions of saturated aqueous NaHCO$_3$ (3×) and brine (1×), dried (MgSO$_4$), and the organic layer concentrated to afford the crude product, which was purified by column chromatography (silica, ethyl acetate). This material was treated with 1M ethereal HCl to afford the hydrochloride (mp 115°-120° C.) as a white solid (150 mg, 19.6%).

EXAMPLE 4

2,3-Dimethyl-5-Oxo-1-Phenyl-3-4-trichloromethylthio-Pyrazoline

To a vigorously stirred solution of 2,3-dimethyl-5-oxo-1-phenyl-3-pyrazolin-4-yl thiocyanate (2.0 g, 8.15 mmol) and triethylbutylammonium chloride (20 mg, 0.09 mmol) in chloroform (5 mL) was added 50% aqueous NaOH solution (1.6 mL). After stirring at 25° C. for 25 minutes, the reaction mixture was refluxed for 45 minutes, then allowed to stir at 25° C. for 17 hours. The reaction mixture was then diluted with CH$_2$Cl$_2$ (75 mL) and washed with H$_2$O (40 mL) and brine (40 mL), then dried (MgSO$_4$) and concentrated to afford the crude product. This material was purified by flash chromatography (silica; ethyl acetate-hexane 1:1) followed by recrystallization (ethyl acetate) to afford light yellow crystals (620 mg), mp 174°-175° C.

2,3-Dimethyl-5-oxo-1-phenyl-4-trifluoromethylthio-3-pyrazoline can be synthesized using the same basic protocol.

EXAMPLE 5

In Vitro Receptor Binding Assay

The potency of the compounds of the invention as inhibitors of the specific binding of radiolabeled CRF to rat cerebral cortex membranes was examined using a standard in vitro radioligand binding technique. Male Sprague-Dawley rats (175-250 g) were sacrificed by decapitation, the cerebral cortex was removed and the tissue homogenized in 20 volumes (w/v) of ice-cold buffer consisting of 50 mM Hepes (N-2-hydroxyethyl-piperazine-N'-2-ethanesulfonic acid) containing 10 mM MgCl, and 2 mM EGTA [ethylene glycol bis-($\beta$-aminoethyl ether) N,N,N',N'-tetraacetic acid]; pH 7.0 at 20° C.) using a Brinkman Polytron (15-20 seconds at setting 5.5). The homogenate was centrifuged at 48,000 × g for 10 minutes at 4° C. The supernatant was removed, the tissue pellet suspended in the original volume of fresh homogenization buffer using a Polytron and centrifuged as before. The final tissue pellet was suspended to a concentration of 11.25 mg tissue (wet weight) per mL of incubation buffer. Incubation buffer consists of 50 mM Hepes (pH 7.0 at 22° C.) containing 10 mM MgCl$_2$, 2 mM EGTA, 0.1 mM bacitracin, 100 KIU (kallikrein inhibitor units)/mL aprotinin and 0.1% BSA (bovine serum albumin). Two hundred $\mu$L of the tissue homogenate was added to 1.5 mL polypropylene microfuge tubes containing 100 $\mu$L of [$^{125}$I] tyrosine-oCRF (final concentration of 50-100 pM; specific activity=2,200 uCi/mmol; DuPont NEN), 100 $\mu$L of the incubation buffer and 100 $\mu$L of the test compound or 100 $\mu$l of unlabeled oCRF (Peninnsula Laboratories). Nonspecific binding was determined in the presence of 1 $\mu$M oCRF. The binding reaction was allowed to proceed for 2 hours at room temperature. Bound radioligand was separated from the incubation medium by centrifugation in a Beckman microfuge for 5 minutes at 12,000 × g. The supernatant was aspirated and the resulting pellet was washed with 1 mL of cold phosphate buffered saline (pH 7.2) containing 0.01% of Triton X-100. The contents were centrifuged as before and radioactivity in the resulting pellet was measured in a gamma counter (LKB RIAGamma 1274) at an efficiency of 80%.

The potency of compounds to inhibit the specific binding of [$^{125}$I] Tyr-oCRF to rat cortical membranes was determined on at least three separate occasions using 8-10 concentrations of each compound and utilizing triplicate incubations. The IC$_{50}$ and apparent Hill coefficient for each compound were calculated using a computer-assisted log-logit analysis.

The results are reported in the tables that follow Example 6.

EXAMPLE 6

Inhibition of CRF-Stimulated Adenylate Cyclase Activity

Male Sprague-Dawley rats (175-250 g) were sacrificed by decapitation, the frontal cortex was dissected and homogenized in 30 volumes (w/v) of ice-cold buffer (50 mM Tris HCl, 10 mM MgCl$_2$, 2 mM EGTA; pH 7.2 at 22° C.). The homogenate was centrifuged at 40,000 × g for 3 minutes (4° C.), the supernatant discarded and the pellet resuspended in original volume of fresh homogenization buffer. Following centrifugation at 40,000 × g for 30 minutes, the resulting pellet was suspended to a tissue concentration of 20 mg original wet weight of tissue per mL (approximately 40-60 $\mu$g protein/mL). For determination of basal adenylate cyclase activity, assays are carried out at 37° C. for 10 minutes in 250 $\mu$L of buffer containing 100 mM Tris HCl, 10 mM MgCl$_2$, 0.4 mM EGTA, 0.1% BSA, 1 mM isobutylmethylxanthine (IBMX), 3 units/tube phosphocreatine kinase, 5 mM creatine phosphate, 100 $\mu$M guanosine. Maximal stimulation of adenylate cyclase activity was accomplished by the addition of 10$^{-6}$M oCRF. Stimulated enzyme activity generally represented a 75-95% increase over basal levels. Reactions were initiated by the addition of tissue and terminated by the addition of 150 $\mu$L of 50 mM Tris HCl, 45 mM ATP, 2% sodium dodecyl sulfate (SDS), and [$^3$H] cAMP (approximately 40,000 dpm). The [$^3$H]cAMP was added to each assay tube to monitor recovery of cAMP during subsequent chromatography steps. Separation of [$^{32}$P]cAMP from [$^{32}$P]ATP was accomplished by sequential elution over Dowex and alumina columns. The eluate (4 mL) was collected in 20 mL scintillation vials to which 8 mL of Beckman EP fluor was added. Vials were shaken for 30 minutes prior to measuring $^3$H and $^{32}$P by scintillation counting. All data were fed directly from the liquid scintillation counter via RS232 port to a VAX 8300 computer. Individual data points were expressed as pmoles of cAMP formed/10 minutes/mg protein. Protein content of tissue samples was measured using the BioRad method with bovine serum albumin serving as the standard.

Determination of antagonist activity was accomplished by addition of at least six concentrations of the compound (10$^{-8}$–10$^{-4}$M), evaluated in triplicate, in the presence of a maximally stimulating concentration of oCRF (1 $\mu$M). IC$_{50}$ values were derived from a log-logit transformation of the data on a Vax 8300.

The results are presented in the tables that follow.

TABLE I

CRF Receptor Affinity and Antagonist Activity of 4-Substituted Thio-5-Oxo-3-Pyrazolines of Formula I

| Inhibition of CRF Binding, Rat Cerebral Cortex Membrane, IC$_{50}$, $\mu$M (N)* | Inhibition of CRF Stimulated Adenylate Cyclase Activity IC$_{50}$, $\mu$M (N)* | R$_1$ | R$_2$ | R$_3$ | R$_4$ |
|---|---|---|---|---|---|
| 3.8 (4) | 3.6 (3) | 2-Naphthyl | CH$_3$ | CH$_3$ | SCN |
| 4.9 (3) | 1.4 (3) | 3,4 Cl$_2$Ph | C$_2$H$_5$ | CH$_3$ | SCN |
| 5.7 (7) | 2.0 (4) | 4-NO$_2$Ph | C$_2$H$_5$ | CH$_3$ | SCN |
| 6.5 (3) | 3.0 (3) | Ph | CH$_3$ | 3-AcNHPh | SCN |
| 6.5 (3) | — | 4-IPh | CH$_3$ | CH$_3$ | SCN |
| 7.4 (3) | 6.9 (3) | 3-ClPh | C$_2$H$_5$ | CH$_3$ | SCN |
| 8.6 | 9.1 | 4-CH$_3$Ph | CH$_3$ | CH$_3$ | SCN |

TABLE I-continued

CRF Receptor Affinity and Antagonist Activity of
4-Substituted Thio-5-Oxo-3-Pyrazolines of Formula I

| Inhibition of CRF Binding, Rat Cerebral Cortex Membrane, $IC_{50}$, $\mu M$ (N)* | Inhibition of CRF Stimulated Adenylate Cyclase Activity $IC_{50}$, $\mu M$ (N)* | $R_1$ | $R_2$ | $R_3$ | $R_4$ |
|---|---|---|---|---|---|
| 9.3 (4) | 11.9 (3) | 4-OMePh | $CH_3$ | $C_2H_5$ | SCN |
| 12.2 (3) | 6.5 (3) | Ph | $C_2H_5$ | $CH_3$ | SCN |
| 13.7 (4) | 2.9 (3) | Ph | $CH_3$ | $CH_3$ | SAc |
| 14.4 (3) | 49.6 (2) | Ph | $CH_3$ | $NH_2$ | SCN |
| 15.5 (3) | 6.9 (3) | 3-CNPh | $CH_3$ | $CH_3$ | SCN |
| 15.0 (4) | 35.2 (3) | $C_6H_{11}$ | $CH_3$ | $CH_3$ | SCN |
| 16.0 (3) | 19.5 (3) | Ph | $CH_3$ | $CH_3$ | SCN |
| 16.1 (17) | 6.1 (5) | Ph | Ph | $CH_3$ | SCN |
| 17.0 (3) | 11.4 (3) | 4-$CH_3SO_2$Ph | $C_2H_5$ | $CH_3$ | SCN |
| 17.0 (3) | 39.9 (3) | $CH_2$Ph | $CH_2CH_3$ | $CH_3$ | SCN |
| 18.9 (3) | 29.9 (3) | 2,6-$Cl_2$Ph | $CH_3$ | $CH_3$ | SCN |
| 19.1 (3) | 31.7 (3) | Ph | $CH_3$ | $CH_2CH_3$ | SCN |
| 20.4 (5) | 9.6 (4) | Ph | $CH_3$ | $CH_3$ | $SCCl_3$ |
| 32.0 (3) | 16.9 (3) | Ph | $(CH_2)_2CH_3$ | $CH_3$ | SCN |
| 32.0 (4) | 69.3 (3) | H | 4-$NO_2$Ph | $CH_3$ | SCN |
| 33.6 (4) | 40.1 (3) | $CH_3$ | $CH_2$Ph | $CH_3$ | SCN, Fumarate |
| 39.8 (2) | — (1) | Ph | $CH_3$ | MorCH_2** | SCN |
| 67.0 (3) | 45.0 (3) | $C_2H_5$ | $C_2H_5$ | $C_2H_5$ | SCN |
| 111.0 (4) | 29.4 (4) | $C_2H_5$ | $C_2H_5$ | $CH_3$ | SCN |

*N = Number of determinations
**MorCH_2 = morpholinomethyl

TABLE II

CRF Receptor Affinity and Antagonist Activity of
4-Substituted Thio-5-Oxo-3-Pyrazolines of Formula II

| Inhibition of CRF Binding, Rat Cerebral Cortex Membrane, $IC_{50}$, $\mu M$ (N)* | Inhibition of CRF Stimulated Adenylate Cyclase Activity $IC_{50}$, $\mu M$ (N)* | $R_1$ | $R_2$ | $R_3$ | Salt |
|---|---|---|---|---|---|
| 2.2 (4) | 1.1 (1) | Ph | $CH_3$ | $CH_3$ | |
| 2.9 (3) | 4.3 (3) | 3,4-$Cl_2$Ph | $C_2H_5$ | $CH_3$ | |
| 3.3 (2) | 3.3 (3) | Ph | $CH_3$ | $C_2H_5$ | |
| 3.3 (3) | 1.0 (2) | 2-Naphthyl | $CH_3$ | $CH_3$ | HCl |
| 4.3 (3) | 3.8 (3) | $CH_2$Ph | $C_2H_5$ | $CH_3$ | |
| 4.3 (3) | — | 6-Cl-2-Pyr | $CH_3$ | $CH_3$ | |
| 4.8 (4) | 1.0 (1) | Ph | $C_2H_5$ | $CH_3$ | |
| 5.1 (1) | — | 4-IPh | $CH_3$ | $CH_3$ | |
| 6.4 (3) | 2.5 (3) | Ph | $CH_3$ | $CH_3$ | HCl |
| 8.2 (3) | 1.5 (2) | Ph | $CH_3$ | MorCH_2** | 2HCl |

*N = Number of determinations
**MorCH_2 = morpholinomethyl

What is claimed is:

1. A corticotropoin-releasing factor antagonist represented by the Formula I:

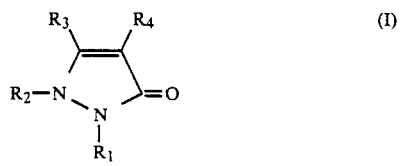

wherein:
- $R_1$ is hydrogen; phenyl; phenyl singly or multiply substituted with halogen, nitro, amino, alkylamino, dialkylamino, dialkylaminomethyl, $C_{1-8}$alkyl (straight chain, branched, saturated or unsaturated), hydroxy, alkoxy, cyano, trifluoromethyl, alkylthio, alkylsulfonyl, or methylenedioxy; naphthyl; indanyl; indenyl; $C_{1-4}$alkyl (straight chain, branched, saturated or unsaturated); or aralkyl (where the aryl group is selected from phenyl or naphthyl and the alkyl group is $C_{1-3}$);
- $R_2$ is $C_{1-4}$alkyl (straight chain, branched, saturated or unsaturated); phenyl; or aralkyl (where the aryl group is selected from those set forth in the definition of $R_1$ and the alkyl is $C_{1-3}$);
- $R_3$ is $C_{1-8}$ alkyl (straight chain, branched, saturated or unsaturated); $C_{1-8}$ straight chain alkyl substituted with at least one carboxylic acid, amino or carboxymethoxy group; phenyl; or phenyl singly or multiply substituted with acetimido, amino, nitro, alkylamino, dialkylaminomethyl, hydroxy, alkoxy, alkylsulfonyl, methylenedioxy, halogen or trifluoromethyl;
- $R_4$ is $SCO\text{-}C_{1-4}$alkyl, or pharmaceutically acceptable salt thereof.

2. The corticotropin-releasing factor antagonist according to claim 1 wherein said alkylamino, dialkylamino, dialkylaminomethyl, alkoxy, alkylthio and alkylsulfonyl substituents are $C_{1-4}$.

3. The corticotropin-releasing factor antagonist according to claim 1 wherein
- $R_1$ is phenyl
- $R_2$ and $R_3$ are methyl; and
- $R_4$ is $SCOCH_3$.

4. The compound 2,3-dimethyl-5-oxo-1-phenyl-3-pyrazolin-4-yl thioacetate, or pharmaceutically acceptable salt thereof.

5. A pharmaceutical composition in dosage unit form suitable for use in producing a corticotropin releasing factor antagonistic effect in an animal comprising, as an active ingredient, an amount of at least one 4-substituted thio-5-oxo-3-pyrazoline, or pharmaceutically acceptable salt thereof, sufficient to produce said effect, said 4-substituted thio-5-oxo-3-pyrazoline being a corticotropin-releasing factor antagonist of claim 1, together with a pharmaceutically acceptable carrier.

6. A pharmaceutical composition in dosage unit form suitable for use in producing a corticotropin releasing factor antagonistic effect in an animal comprising, as an active ingredient, an amount of 2,3-dimethyl-5-oxo-1-phenyl-3-pyrazolin-4-yl thioacetate, or pharmaceutically acceptable salt thereof, sufficient to exert said effect, together with a pharmaceutically acceptable carrier.

7. The pharmaceutical composition according to one of claims 5, or 6 wherein said composition is in capsule, tablet, powder or granule form.

8. The pharmaceutical composition according to one of claims 5, or 6 wherein said composition is in the form of a sterile injectable solution.

* * * * *